US009579651B2

(12) United States Patent
Phan et al.

(10) Patent No.: US 9,579,651 B2
(45) Date of Patent: Feb. 28, 2017

(54) BIOLOGIC FLUID ANALYSIS CARTRIDGE

(75) Inventors: Vu Phan, Princeton, NJ (US); John A. Verrant, Solebury, PA (US); John Blum, Somerset, NJ (US); Kaushal K. Verma, Franklin Park, NJ (US); Elise G. Edson, Somerset, NJ (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 12/971,860

(22) Filed: Dec. 17, 2010

(65) Prior Publication Data

US 2011/0206557 A1 Aug. 25, 2011

Related U.S. Application Data

(60) Provisional application No. 61/287,955, filed on Dec. 18, 2009, provisional application No. 61/291,121, filed on Dec. 30, 2009.

(51) Int. Cl.
*G01N 33/00* (2006.01)
*B01L 3/00* (2006.01)
(Continued)

(52) U.S. Cl.
CPC ........ *B01L 3/50273* (2013.01); *B01F 5/0614* (2013.01); *B01F 5/0618* (2013.01); *B01F 5/0646* (2013.01); *B01F 5/0647* (2013.01); *B01F 5/0652* (2013.01); *B01F 13/0059* (2013.01); *B01L 3/502707* (2013.01); *B01F 2005/0632* (2013.01); *B01L 2200/027* (2013.01); *B01L 2200/028* (2013.01); *B01L 2200/0621* (2013.01);
(Continued)

(58) Field of Classification Search
CPC ............ B01L 3/50273; B01L 2200/27; B01L 2400/406
See application file for complete search history.

(56) References Cited

U.S. PATENT DOCUMENTS 3,447,863 A 6/1969 Patterson
3,883,247 A 5/1975 Adams
(Continued)

FOREIGN PATENT DOCUMENTS

EP 0381501 8/1990
EP 0638799 2/1995 .......................... 21/5
(Continued)

OTHER PUBLICATIONS

International Search Report for PCT/US10/61080, Jun. 29, 2011.
Office action for CN201080063961.7 dated Dec. 23, 2013.

*Primary Examiner* — Sam P Siefke
(74) *Attorney, Agent, or Firm* — O'Shea Getz P.C.

(57) ABSTRACT

A biological fluid sample analysis cartridge is provided. The cartridge includes a housing, a fluid module, and an analysis chamber. The fluid module includes a sample acquisition port and an initial channel, and is connected to the housing. The initial channel is sized to draw fluid sample by capillary force, and is in fluid communication with the acquisition port. The initial channel is fixedly positioned relative to the acquisition port such that at least a portion of a fluid sample disposed within the acquisition port will draw into the initial channel. The analysis chamber is connected to the housing, and is in fluid communication with the initial channel.

13 Claims, 8 Drawing Sheets

(51) Int. Cl.
*B01F 5/06* (2006.01)
*B01F 13/00* (2006.01)

(52) U.S. Cl.
CPC . *B01L 2300/045* (2013.01); *B01L 2300/0816* (2013.01); *B01L 2300/0867* (2013.01); *B01L 2400/0406* (2013.01); *B01L 2400/0478* (2013.01); *B01L 2400/0481* (2013.01); *B01L 2400/0487* (2013.01); *B01L 2400/065* (2013.01); *B01L 2400/0633* (2013.01); *B01L 2400/0655* (2013.01)

(56) References Cited

U.S. PATENT DOCUMENTS 3,895,661 A 7/1975 Praglin et al.
3,916,205 A 10/1975 Kleinerman
3,925,166 A 12/1975 Blume
4,088,448 A 5/1978 Lilja et al.
4,171,866 A 10/1979 Tolles
4,264,560 A 4/1981 Natelson
4,427,294 A 1/1984 Nardo
4,550,417 A 10/1985 Nunogaki et al.
4,558,014 A 12/1985 Hirschfield et al.
4,596,035 A 6/1986 Gershman et al.
4,689,307 A 8/1987 Schwartz
4,790,640 A 12/1988 Nason
4,853,210 A 8/1989 Kass
4,902,624 A 2/1990 Columbus et al.
4,911,782 A 3/1990 Brown
4,950,455 A 8/1990 Smith
5,028,529 A 7/1991 Ericcson
5,096,669 A * 3/1992 Lauks et al. ............. 204/403.02
5,122,284 A 6/1992 Braynin et al.
5,132,097 A 7/1992 Van Deusen et al.
5,169,601 A 12/1992 Ohta et al.
5,184,188 A 2/1993 Bull et al.
5,223,219 A 6/1993 Subramanian et al.
5,275,951 A 1/1994 Chow et al.
5,281,540 A 1/1994 Merkh et al.
5,316,952 A 5/1994 Brimhall
5,362,648 A 11/1994 Koreyasu et al.
5,376,252 A 12/1994 Ekstrom et al.
5,397,479 A 3/1995 Kass et al.
5,427,959 A 6/1995 Nishimura et al.
5,431,880 A 7/1995 Kramer
5,472,671 A 12/1995 Nilsson et al.
5,482,829 A 1/1996 Kass et al.
5,503,803 A 4/1996 Brown
5,538,691 A 7/1996 Tosa et al.
5,547,849 A 8/1996 Baer et al.
5,585,246 A 12/1996 Dubrow et al.
5,591,403 A 1/1997 Gavin et al.
5,608,519 A 3/1997 Gourley et al.
5,623,415 A 4/1997 O'Bryan et al.
5,627,041 A 5/1997 Shartle
5,638,828 A 6/1997 Lauks et al.
5,641,458 A 6/1997 Shockley, Jr. et al.
5,646,046 A 7/1997 Fischer
5,674,457 A 10/1997 Williamsson et al.
5,681,529 A 10/1997 Taguchi et al.
5,768,407 A 6/1998 Shen et al.
5,781,303 A 7/1998 Berndt
5,787,189 A 7/1998 Lee et al.
5,800,781 A 9/1998 Gavin et al.
5,879,628 A 3/1999 Ridgeway et al.
5,939,326 A 8/1999 Chupp et al.
5,948,686 A 9/1999 Wardlaw
5,968,453 A 10/1999 Shugart
5,985,218 A 11/1999 Goodale
6,004,821 A 12/1999 Levine et al.
6,016,367 A 1/2000 Benedetti et al.
6,016,712 A 1/2000 Warden et al.
6,022,734 A 2/2000 Wardlaw
6,106,778 A 8/2000 Oku et al.
6,130,098 A 10/2000 Handique et al.
6,150,178 A 11/2000 Cesarczyk et al.
6,176,962 B1 1/2001 Soane et al.
6,188,474 B1 2/2001 Dussault et al.
6,235,536 B1 5/2001 Wardlaw
6,261,519 B1 7/2001 Harding et al.
6,365,111 B1 4/2002 Bass
6,395,232 B1 5/2002 McBride
6,420,114 B1 7/2002 Bedilion et al.
6,448,090 B1 9/2002 McBride
6,468,807 B1 10/2002 Svensson et al.
6,521,182 B1 2/2003 Shartle et al.
6,537,501 B1 3/2003 Holl et al.
6,544,793 B2 4/2003 Berndt
6,551,554 B1 4/2003 Vermeiden et al.
6,573,988 B1 6/2003 Thomsen et al.
6,576,194 B1 6/2003 Holl et al.
6,597,438 B1 7/2003 Cabuz et al.
6,613,286 B2 9/2003 Braun, Sr. et al.
6,613,529 B2 9/2003 Bedilion et al.
6,623,701 B1 9/2003 Eichele et al.
6,656,431 B2 12/2003 Holl et al.
6,712,925 B1 3/2004 Holl et al.
6,723,290 B1 4/2004 Wardlaw
6,766,817 B2 7/2004 da Silva
6,783,736 B1 8/2004 Taylor et al.
6,838,055 B2 1/2005 Sando et al.
6,852,284 B1 2/2005 Holl et al.
6,866,823 B2 3/2005 Wardlaw
6,974,692 B2 12/2005 Chang
7,000,330 B2 2/2006 Schwichtenberg et al.
7,010,391 B2 3/2006 Handique et al.
7,220,593 B2 5/2007 Haubert et al.
7,226,562 B2 6/2007 Holl et al.
7,277,166 B2 10/2007 Padmanabhan et al.
7,329,538 B2 2/2008 Wainwright et al.
7,351,379 B2 4/2008 Schleifer
7,364,699 B2 4/2008 Charlton
7,381,374 B2 6/2008 Tsai et al.
7,468,160 B2 12/2008 Thompson et al.
7,641,856 B2 1/2010 Padmanabhan et al.
7,671,974 B2 3/2010 O'Mahony et al.
7,731,901 B2 6/2010 Wardlaw
7,738,094 B2 6/2010 Goldberg
7,744,819 B2 6/2010 Berndtsson et al.
7,794,669 B2 9/2010 Gyonouchi et al.
7,802,467 B2 9/2010 Wang
7,871,813 B2 1/2011 Wyatt et al.
7,903,241 B2 3/2011 Wardlaw et al.
7,929,122 B2 4/2011 Wardlaw et al.
7,951,337 B2 5/2011 Vollert
7,951,599 B2 5/2011 Levine et al.
7,976,789 B2 7/2011 Kenis et al.
7,978,329 B2 7/2011 Padmanabhan et al.
8,025,854 B2 9/2011 Ohman et al.
8,033,162 B2 10/2011 Wang
8,071,051 B2 12/2011 Padmanabhan et al.
8,092,758 B2 1/2012 Lindberg et al.
8,097,225 B2 1/2012 Padmanabhan et al.
8,133,738 B2 3/2012 Levine et al.
8,158,434 B2 4/2012 Wardlaw
8,163,165 B2 4/2012 Offenbacher et al.
8,173,380 B2 5/2012 Yang et al.
2002/0025279 A1 2/2002 Weigl
2003/0012697 A1 1/2003 Hahn et al.
2006/0160164 A1 7/2006 Miller et al.
2006/0250604 A1 11/2006 Hamada et al.
2007/0025876 A1 2/2007 Nishijima et al.
2007/0036679 A1 2/2007 Munenaka
2007/0111302 A1 5/2007 Handique et al.
2007/0243117 A1 10/2007 Wardlaw
2007/0254372 A1 11/2007 Bickel et al.
2008/0176253 A1 7/2008 Christodoulides et al.
2008/0200343 A1 8/2008 Clemens et al.
2009/0011518 A1 1/2009 Lindberg
2009/0156966 A1 6/2009 Kontschieder
2009/0286327 A1 11/2009 Cho et al.
2010/0021456 A1 1/2010 Miossec et al.
2010/0175999 A1 7/2010 Barlow et al.
2010/0189338 A1 7/2010 Lin et al.

(56) References Cited

U.S. PATENT DOCUMENTS

| | | | | |
|---|---|---|---|---|
| 2010/0209304 | A1 | 8/2010 | Sarofim | |
| 2011/0026009 | A1* | 2/2011 | Knutson et al. | 356/39 |
| 2011/0044862 | A1 | 2/2011 | Chang et al. | |
| 2011/0136152 | A1 | 6/2011 | Lin et al. | |
| 2011/0164803 | A1 | 7/2011 | Wang et al. | |
| 2011/0192219 | A1 | 8/2011 | Miyamura | |
| 2011/0214745 | A1 | 9/2011 | Zhou et al. | |
| 2011/0244581 | A1 | 10/2011 | Nikonorov et al. | |
| 2011/0293489 | A1 | 12/2011 | Zhou et al. | |
| 2012/0004139 | A1 | 1/2012 | Staker | |
| 2012/0034647 | A1 | 2/2012 | Herzog et al. | |
| 2012/0082599 | A1 | 4/2012 | Weber | |

FOREIGN PATENT DOCUMENTS

| | | | |
|---|---|---|---|
| EP | 0778950 | 6/1997 | |
| EP | 0788604 | 8/1997 | |
| EP | 1245279 | 10/2002 | |
| EP | 1390750 | 2/2004 | |
| EP | 1701150 | 9/2006 | |
| EP | 1932594 | 6/2008 | |
| EP | 2040839 | 4/2009 | |
| EP | 2050498 | 3/2012 | |
| WO | WO 95/11454 | 4/1995 | 33/50 |
| WO | 9624876 | 8/1996 | |
| WO | 9945386 | 9/1999 | |
| WO | 0132828 | 5/2001 | |
| WO | 2005100539 | 10/2005 | |
| WO | 2005111580 | 11/2005 | |
| WO | 2005114142 | 12/2005 | |
| WO | 2006124821 | 11/2006 | |
| WO | 2007047908 | 4/2007 | |
| WO | 2007075922 | 7/2007 | |
| WO | 2007084232 | 7/2007 | |
| WO | 2007112332 | 10/2007 | |
| WO | WO 2008034102 * | 3/2008 | |
| WO | 2008079616 | 7/2008 | |
| WO | 2008087405 | 7/2008 | |
| WO | 2008157795 | 12/2008 | |
| WO | 2009117652 | 9/2009 | |
| WO | 2009117664 | 9/2009 | |
| WO | 2009117682 | 9/2009 | |
| WO | 2009117683 | 9/2009 | |
| WO | 2009124179 | 10/2009 | |
| WO | 2009124186 | 10/2009 | |
| WO | 2009124190 | 10/2009 | |
| WO | 2009126505 | 10/2009 | |
| WO | 2009126800 | 10/2009 | |
| WO | 2011075667 | 6/2011 | |
| WO | 2011082342 | 7/2011 | |
| WO | 2011116305 | 9/2011 | |
| WO | 2012004723 | 1/2012 | |
| WO | 2012019118 | 2/2012 | |

* cited by examiner

BIOLOGIC FLUID ANALYSIS CARTRIDGE

The present application is entitled to the benefit of and incorporates by reference essential subject matter disclosed in the following U.S. Provisional Patent Applications: Ser. Nos. 61/287,955, filed Dec. 18, 2009; and 61/291,121, filed Dec. 30, 2009.

BACKGROUND OF THE INVENTION

1. Technical Field

The present invention relates to apparatus for biologic fluid analyses in general, and to cartridges for acquiring, processing, and containing biologic fluid samples for analysis in particular.

2. Background Information

Historically, biologic fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the cell integrity, accuracy and reliability of the data depends largely on the technician's experience and technique.

Another known method for evaluating a biologic fluid sample involves diluting a volume of the sample, placing it within a chamber, and manually evaluating and enumerating the constituents within the diluted sample. Dilution is necessary if there is a high concentration of constituents within the sample, and for routine blood counts several different dilutions may be required because it is impractical to have counting chambers or apparatus which can examine variable volumes as a means to compensate for the disparities in constituent populations within the sample. In a sample of whole blood from a typical individual, for example, there are about $4.5\times10^6$ red blood cells (RBCs) per microliter (μl) of blood sample, but only about $0.25\times10^6$ of platelets and $0.007\times10^6$ white blood cells (WBCs) per μl of blood sample. To determine a WBC count, the whole blood sample must be diluted within a range of about one part blood to twenty parts diluent (1:20) up to a dilution of approximately 1:256 depending upon the exact dilution technique used, and it is also generally necessary to selectively lyse the RBCs with one or more reagents. Lysing the RBCs effectively removes them from view so that the WBCs can be seen. To determine a platelet count, the blood sample must be diluted within a range of 1:100 to about 1:50,000. Platelet counts do not, however, require a lysis of the RBCs in the sample. Disadvantages of evaluating a whole blood sample in this manner include the dilution process is time consuming and expensive, increased error probability due to the diluents within the sample data, etc.

Another method for evaluating a biologic fluid sample is impedance or optical flow cytometry, which involves circulating a diluted fluid sample through one or more small diameter orifices, each employing an impedance measurement or an optical system that senses the different constituents in the form of scattered light as they pass through the hydrodynamically focused flow cell in single file. In the case of whole blood, the sample must be diluted to mitigate the overwhelming number of the RBCs relative to the WBCs and platelets, and to provide adequate cell-to-cell spacing and minimize coincidence so that individual cells may be analyzed. Disadvantages associated with flow cytometry include the fluid handling and control of a number of different reagents required to analyze the sample which can be expensive and maintenance intensive.

Another modern method for evaluating biologic fluid samples is one that focuses on evaluating specific subtypes of WBCs to obtain a total WBC count. This method utilizes a cuvette having an internal chamber about 25 microns thick with one transparent panel. Light passing through the transparent panel scans the cuvette for WBCs. Reagents inside the cuvette cause WBCs to fluoresce when excited by the light. The fluorescing of the particular WBCs provides an indication that particular types of WBCs are present. Because the red blood cells form a partly obscuring layer in this method, they cannot themselves be enumerated or otherwise evaluated, nor can the platelets.

What is needed is a method and an apparatus for evaluating a sample of substantially undiluted biologic fluid, one capable of providing accurate results, one that does not use a significant volume of reagent(s), one that does not require sample fluid flow during evaluation, one that can perform particulate component analyses, and one that is cost-effective.

DISCLOSURE OF THE INVENTION

According to an aspect of the present invention, a biological fluid sample analysis cartridge is provided. The cartridge includes a housing, a fluid module, and an analysis chamber. The fluid module includes a sample acquisition port and an initial channel, and is connected to the housing. The initial channel is sized to draw fluid sample by capillary force, and is in fluid communication with the acquisition port. The initial channel is fixedly positioned relative to the acquisition port such that at least a portion of a fluid sample disposed within the acquisition port will draw into the initial channel. The analysis chamber is connected to the housing, and is in fluid communication with the initial channel.

According to another aspect of the present invention, a biological fluid sample analysis cartridge is provided. The cartridge includes a housing, a fluid module, and an imaging tray. The fluid module includes a sample acquisition port and an initial channel. The fluid module is connected to the housing, and the initial channel is in fluid communication with the acquisition port. The imaging tray includes an analysis chamber. The tray is selectively positionable relative to the housing in an open position and a closed position. In the closed position, the analysis chamber is in fluid communication with the initial channel.

According to another aspect of the present invention, a biological fluid sample analysis cartridge is provided. The cartridge includes a sample acquisition port, a channel, one or more flow disruptors, and an analysis chamber. The acquisition port is attached to a panel, and the channel is disposed in the panel. The channel is in fluid communication with the acquisition port. The flow disrupters are disposed within the channel. The analysis chamber in fluid communication with the channel.

The features and advantages of the present invention will become apparent in light of the detailed description of the invention provided below, and as illustrated in the accompanying drawings.

DETAILED DESCRIPTION

Figure 1:
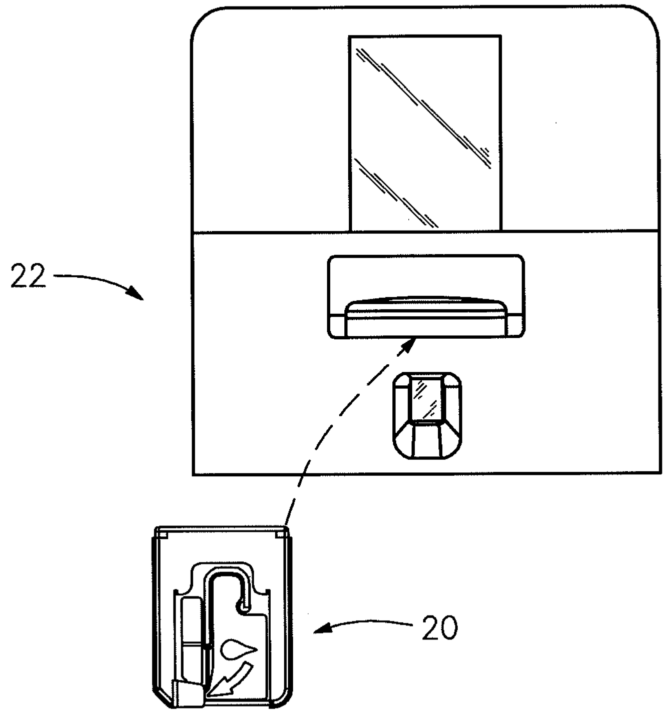
FIG. 1 is illustrates a biologic fluid analysis device.
Figure 2:
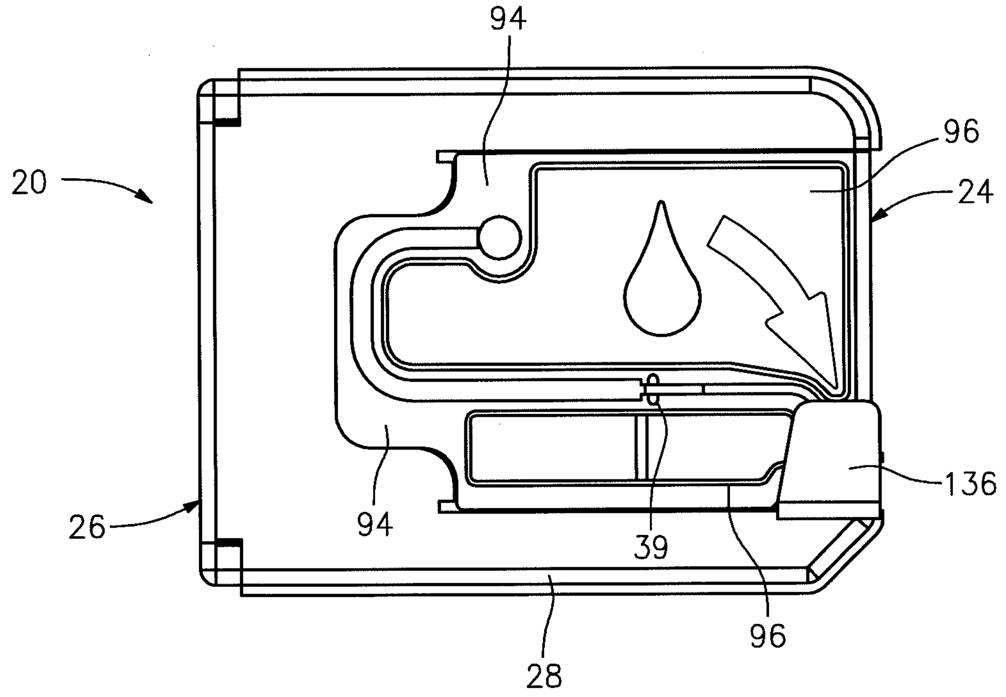
FIG. 2 is a diagrammatic planar view of an embodiment of the present cartridge, illustrating the fluid module and imaging tray in the closed position.
Figure 3:
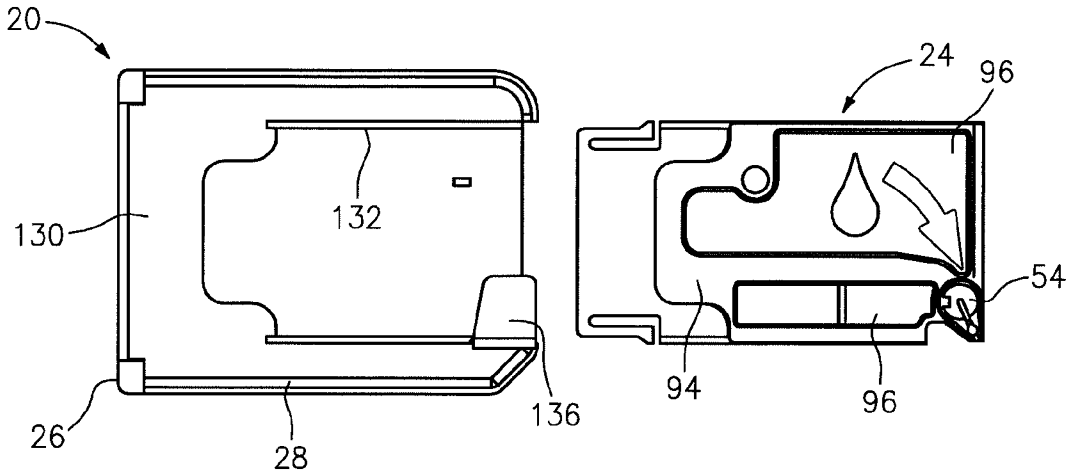
FIG. 3 is an exploded view of the cartridge embodiment, illustrating the fluid module outside of the housing.

Referring to FIG. 1, the present biologic fluid sample cartridge 20 is operable to receive a biologic fluid sample such as a whole blood sample or other biologic fluid specimen. In most embodiments, the cartridge 20 bearing the sample is utilized with an automated analysis device 22 having imaging hardware and a processor for controlling the process and analyzing the images of the sample. An analysis device 22 similar to that described in U.S. Pat. No. 6,866,823 (which is hereby incorporated by reference in its entirety) is an acceptable type of analysis device. The present cartridge 20 is not limited to use with any particular analytical device, however.

Now referring to FIGS. 2-6, the cartridge 20 includes a fluid module 24, an imaging tray 26, and a housing 28. The fluid module 24 and the imaging tray 26 are both connected to the housing 28, each from a transverse end of the housing 28.

The Fluid Module:

Now referring to FIGS. 7-10, a fluid module 24 embodiment includes a sample acquisition port 30, an overflow passage 32, a initial channel 34, a valve 36, a secondary channel 38, one or more latches 40, an air pressure source 42, an external air pressure port 44, and has an exterior edge 46, an interior edge 48, a first lateral side 50, and a second lateral side 52, which lateral sides 50, 52 extend between the exterior edge 46 and the interior edge 48.

The sample acquisition port 30 is disposed at the intersection of the exterior edge 46 and the second lateral side 52. The acquisition port 30 includes one or both of a bowl 54 and an edge inlet 64. The bowl 54 extends between an upper surface 56 and a base surface 58. The acquisition port 30 further includes a sample intake 60, a bowl-to-intake channel 62, and an edge inlet-to-intake channel 66. In alternative embodiments, the acquisition port 30 and the sample intake may be located elsewhere in the fluid module 24; e.g., the acquisition port 30 may be located inwardly from an exterior edge and the sample intake 60 may be positioned in direct communication with the bowl 54 rather than having an intermediary channel connecting the bowl 54 and intake 60.

In the embodiment shown in FIGS. 7-10, the bowl 54 has a parti-spherical geometry. A concave geometry such as that provided by the parti-spherical geometry facilitates gravity collection of the sample within the center of the bowl base surface 58. Other concave bowl geometries include conical or pyramid type geometries. The bowl 54 is not limited to any particular geometry. The volume of the bowl 54 is chosen to satisfy the application for which the cartridge 20 is designed; e.g., for blood sample analysis, a bowl volume of approximately 50 μl will typically be adequate.

The bowl-to-intake channel 62 is disposed in the base surface 58 of the bowl 54, and provides a passage through which fluid deposited into the bowl 54 can travel from the bowl 54 to the sample intake 60. In some embodiments the bowl-to-intake channel 62 has a cross-sectional geometry that causes sample disposed within the channel 62 to be drawn through the channel 62 toward the sample intake 60 by capillary force. For example, the bowl-to-intake channel 62 may have a substantially rectilinear cross-sectional geometry, with a side wall-to-side wall separation distance that allows capillary forces acting on the sample to draw the sample through the channel 62. A portion of the channel 62 adjacent the sample intake 60 includes a curved base surface to facilitate fluid sample flow into the intake 60.

The edge inlet 64 is disposed proximate the intersection of the exterior edge 46 and the second lateral side 52. In the embodiment shown in FIG. 7, the edge inlet 64 is disposed at the end of a tapered projection. The tapered projection provides a visual aid to the end user, identifying where a blood sample from a finger or heel prick, or from a sample drawn from an arterial or venous source, for example, can be drawn into the acquisition port 30. The edge inlet 64 is not required; i.e., some embodiments include only the bowl 54.

The exterior edge inlet-to-intake channel 66 extends between the edge inlet 64 and the sample intake 60. In some embodiments the edge inlet-to-intake channel 66 has a cross-sectional geometry that causes sample disposed within the channel 66 to be drawn through the channel 66 toward the sample intake 60 by capillary force; e.g., a substantially rectilinear cross-sectional geometry, with a side wall separation distance that allows capillary forces acting on the sample to draw the sample through the channel 66. A portion of the channel 66 adjacent the sample intake 60 includes a curved base surface to facilitate fluid sample flow into the intake 60.

The sample intake 60 is a passage that provides fluid communication between the initial channel 34 and the channels 62, 66 extending between the bowl 54 and the edge inlet 64. In the embodiment shown in FIGS. 7-10, the sample intake 60 extends substantially perpendicular to the channels 62, 66. As indicated above, in some embodiments the sample intake 60 may be positioned in direct communication with the bowl 54.

The initial channel 34 extends between the sample intake 60 and the secondary channel 38. The volume of the initial channel 34 is large enough to hold a volume of fluid sample adequate for the analysis at hand, and in some embodiments is large enough to permit mixing of the sample within the initial channel. The cross-sectional geometry of the initial channel 34 is sized to permit sample fluid disposed within the initial channel 34 to be drawn through the channel from the intake 60 via capillary forces. In some embodiments, one or more reagents 67 (e.g., heparin, EDTA, etc.) are deposited within the initial channel 34. As the sample fluid is drawn through the initial channel 34, the reagent 67 is at least partially admixed with the sample. The end of the initial channel 34 opposite the sample intake 60 opens to the secondary channel 38, thereby providing a fluid communication path from the initial channel 34 into the secondary channel 38.

In some embodiments, one or more flag ports 39 (see FIG. 7) extend laterally off of the initial channel 34 proximate the secondary channel 38. The geometry of each flag port 39 is such that sample traveling within the initial channel will encounter the flag port 39 and be drawn in the port 39; e.g., by capillary action. The presence of sample within the port 39 can be sensed to verify the position of the sample within the initial channel 34. Preferably, the flag port 39 has a height that is relatively less than its width to increase the visibility of the sample within the port 39, while requiring only a small fraction of the sample. Each flag port 39 may include an air vent.

Figure 19:
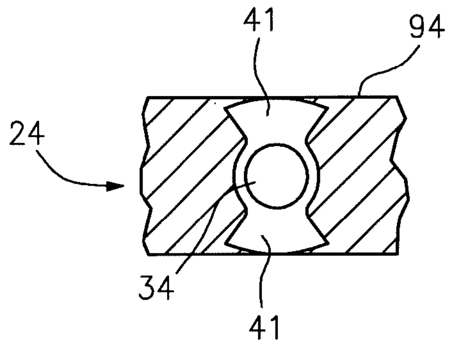
FIG. 19 is a diagrammatic illustration of a sample magnifier disposed relative to the acquisition channel.

In some embodiments, the initial channel 34 (or the flag port 39) includes a sample magnifier 41 (see FIG. 19), preferably disposed proximate the secondary channel 38. The sample magnifier 41 includes a lens disposed on one or both sides of the channel 34 (e.g., on top and bottom). The lens magnifies the aligned portion of the initial channel 34 and thereby facilitates sensing the presence of sample within the initial channel 34. Preferably, the magnification of the lens is strong enough to make sample within the aligned channel section (or port) readily apparent to the end-user's eye.

The secondary channel 38 extends between the initial channel 34 and distal end which can include an exhaust port 68. The cross-sectional geometry of the intersection between the secondary channel 38 and the initial channel 34 is configured such that capillary forces will not draw sample from the initial channel 34 into the secondary channel 38. In some embodiments, the secondary channel 38 includes a sample metering port 72. The secondary channel 38 has a volume that is large enough to permit the movement of sample back and forth within the secondary channel 38, which fluid movement can be used to mix sample constituents and/or reagents within the sample. In some embodiments, a gas permeable and liquid impermeable membrane 74 is disposed relative to the exhaust port 68 to allow air within the secondary channel 38 to exit the channel 38, while at the same time preventing liquid sample from exiting the channel 38 via the port 68.

The sample metering port 72 has a cross-sectional geometry that allows sample to be drawn out of the secondary channel 38 by capillary force. In some embodiments, the volume of the sample metering port 72 is a predetermined volume appropriate for the analysis at hand; e.g., substantially equal to the desired volume of sample for analysis. The metering port 72 extends from the secondary channel 38 to an exterior surface of the tray 24 (which, as will be described below, is aligned with an exterior surface of a panel 122 portion of sample analysis chamber 118 when the tray is in the closed position).

The valve 36 is disposed within the fluid module 24 at a position to prevent fluid flow (including airflow) between a portion of the initial channel 34 and the sample intake 60. The valve 36 is selectively actuable between an open position and a closed position. In the open position, the valve 36 does not impede fluid flow between the sample intake 60 and a portion of the initial channel 34 contiguous with the secondary channel 38. In the closed position, the valve 36 at least substantially prevents fluid flow between at least a portion of the initial channel 34 and the sample intake 60.

Figure 13:
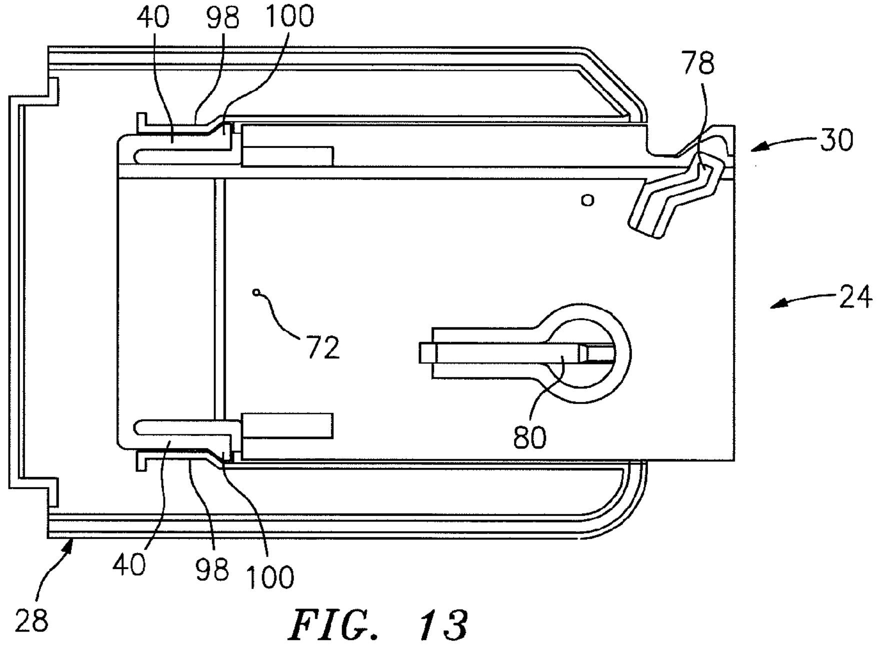
FIG. 13 is a bottom view of a fluid module located within a housing cover, with the fluid module in an open position.
Figure 8:
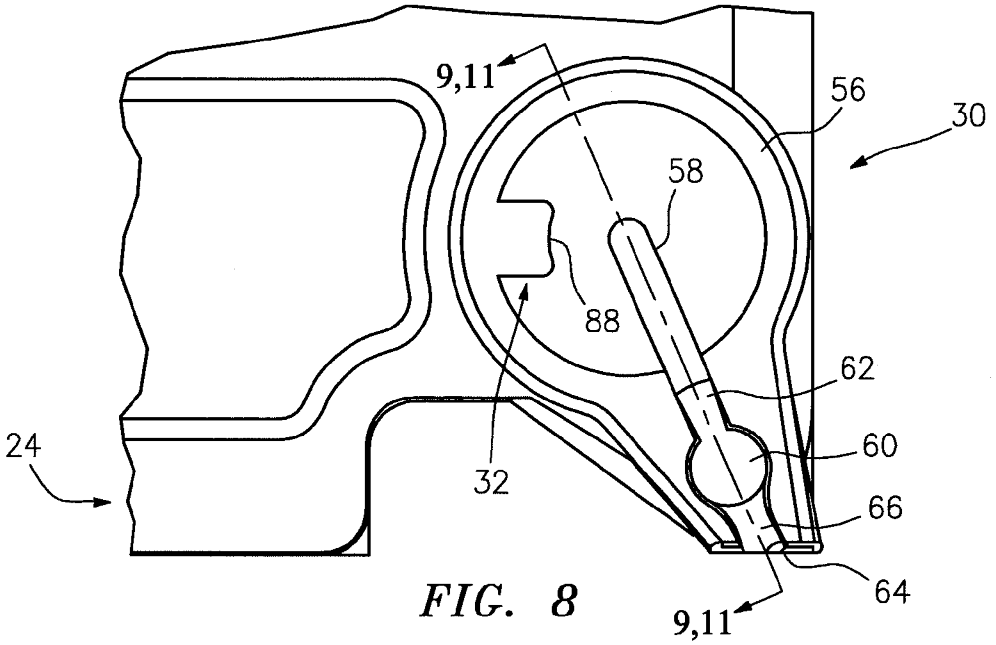
FIG. 8 is a sectional view of a fluid module, including an acquisition port.
Figure 9:
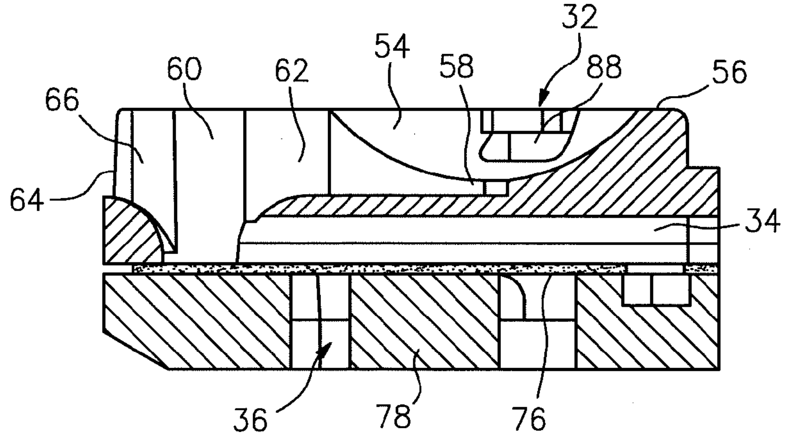
FIGS. 9 and 10 are sectional views of the acquisition port shown in FIG. 8, illustrating a valve embodiment in an open position and a closed position.
Figure 10:
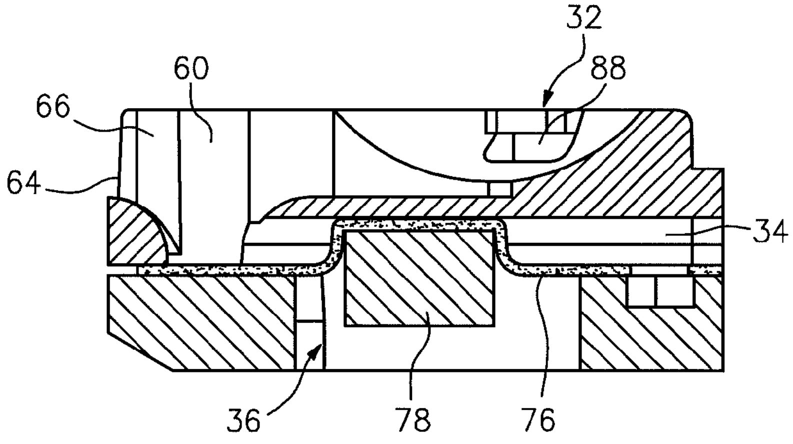
Figure 14:
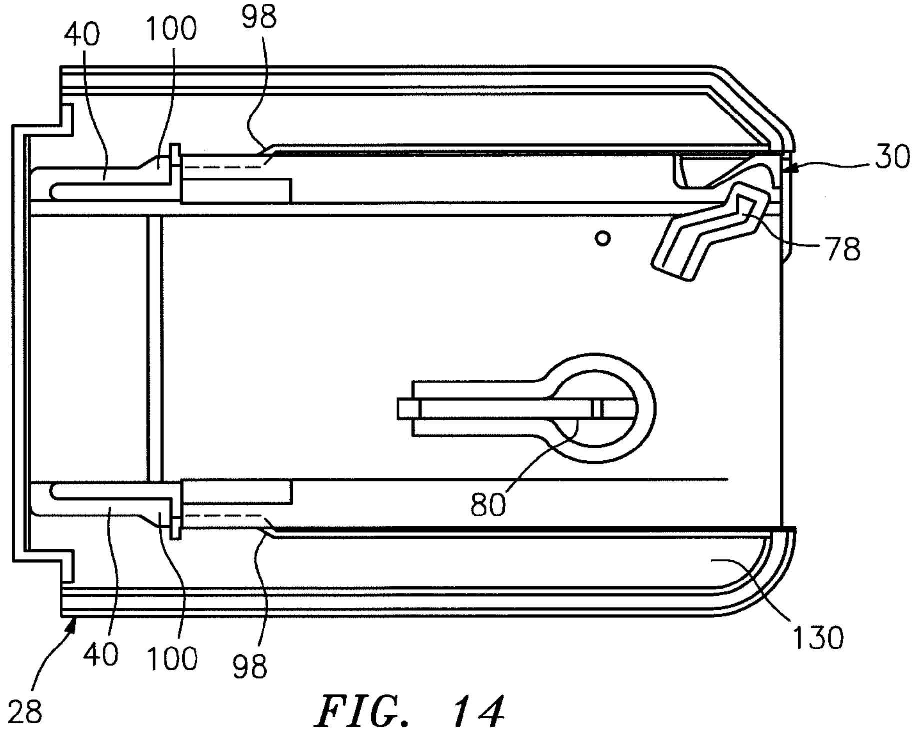
FIG. 14 is a bottom view of a fluid module located within a housing cover, with the fluid module in a closed position.

In the embodiment shown in FIGS. 9 and 10, the valve 36 includes a deflectable membrane 76 (e.g., a hydrophilic pressure sensitive adhesive tape) and a cantilevered valve actuator 78 (see FIGS. 13-14). The actuator 78 can be deflected to move the membrane 76 into communication with the initial channel 34 to create a fluid seal between the channel 34 and the intake 60. FIG. 9 illustrates the valve 36 embodiment in an open position, wherein the fluid path from the sample intake 60 to the initial channel 34 is open. FIG. 10 illustrates the valve 36 embodiment in a closed position, wherein the membrane 76 blocks the fluid path from the sample intake 60 to the initial channel 34 and thereby prevents fluid flow (including airflow) there between. The valve 36 embodiment shown in FIGS. 9 and 10 is an example of an acceptable valve 36 embodiment. The valve 36 is not limited to this embodiment. For example, the valve 36 may alternatively be disposed to act at other positions within the initial channel 34 or the sample intake 60; e.g., any point wherein the volume of the fluid disposed within the portion of the initial channel 34 disposed between the valve 36 and the secondary channel 38 is adequate for the analysis at hand.

Figure 11:
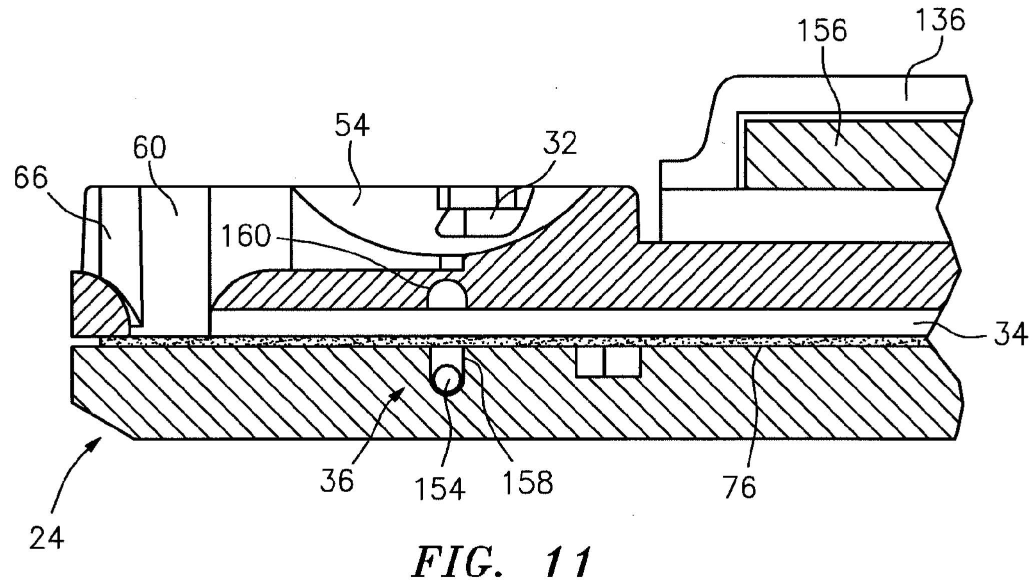
FIGS. 11 and 12 are sectional views of the acquisition port shown in FIG. 8, illustrating a valve embodiment in an open position and a closed position.
Figure 12:
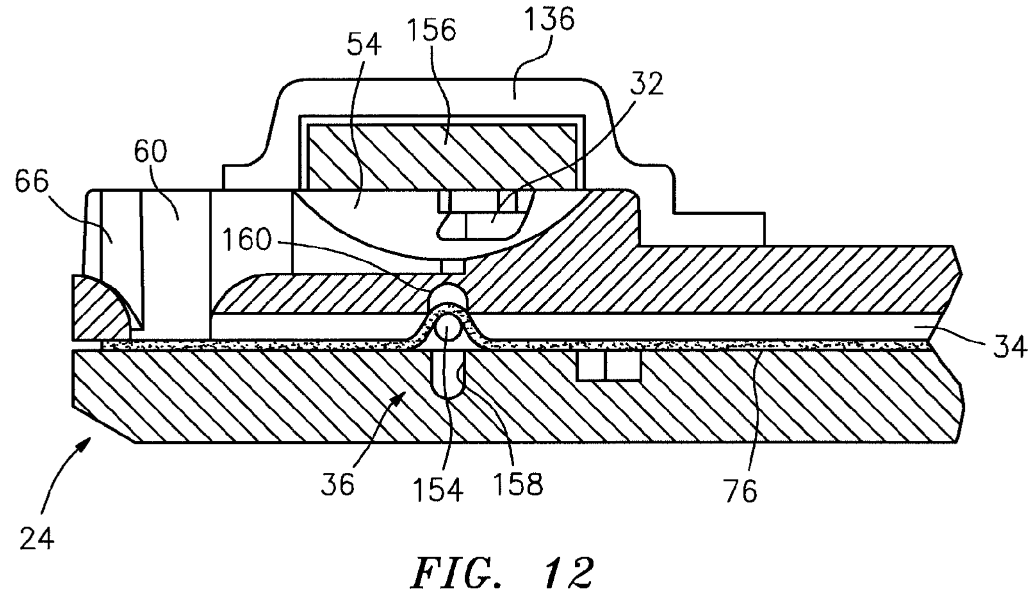

Now referring to FIGS. 11 and 12, in an alternative embodiment, the valve 36 operates between open and closed positions as described above, but the actuation of the valve utilizes a magnetic mechanism rather than a purely mechanical mechanism. In this embodiment, the valve 36 includes a magnetically attractable member 154 (e.g., a steel ball bearing) and a magnet 156 disposed within the bowl cap 136 (see FIG. 11). The fluid module 24 includes a first pocket 158 and a second pocket 160. The first pocket 158 is disposed within the fluid module 24 below the deflectable membrane 76. The second pocket 160 is disposed in the fluid module 24, aligned with first pocket 158, positioned above the deflectable membrane 76 and the initial channel 34. The first and second pockets 158, 160 are substantially aligned with the portion of the fluid module (e.g., the bowl 54) that is aligned with the bowl cap 136 when the fluid module 24 is in the closed position (see FIG. 12). In the absence of magnetic attraction (e.g., when the fluid module 24 is in the open position as is shown in FIG. 11), the member 154 resides within the first pocket 158 and does not deflect the deflectable member 76; i.e., the initial channel 34 is unobstructed. In the fluid module 24 closed position (see FIG. 12), the magnet 156 attracts the member 154, causing it deflect the deflectable member 76 into the second pocket 160. As a result, the deflectable member 76 blocks the initial channel 34 and thereby prevents fluid flow (including airflow) between the sample intake 60 and the initial channel 34. In an alternative embodiment, the magnet 156 is disposed within the fluid module housing 28 and the member 154 and deflectable membrane 76 are disposed in the fluid module 24 above the initial channel 34. In the fluid module closed position, the magnet 156 aligns with the member 154 and draws the magnet 156 and the deflectable membrane 76 downwardly to block the fluid path between the sample intake 60 and the initial channel 34.

In some embodiments, the air pressure source 42 (e.g., see FIG. 7) includes a selectively variable volume (e.g., diaphragm, bladder, etc.) and an actuator 80 (see FIGS. 13-14). The air pressure source 42 contains a predetermined volume of air, and is connected to an airway 82. The airway 82, in turn, is connected to the initial channel 34 at an intersection point that lies between where the valve 36 engages the initial channel 34 and the secondary channel 38. The actuator 80 is operable to compress the volume, and thereby provide pressurized air into the airway and initial channel 34. In the embodiment shown in FIGS. 13-14, the actuator 80 is connected to the fluid module 24 in a cantilevered configuration, wherein a force applied to the actuator 80 causes the free end to compress the source volume. The aforesaid air pressure source 42 embodiment is an example of an acceptable source of pressurized air. The present invention is not limited thereto.

Figure 7:
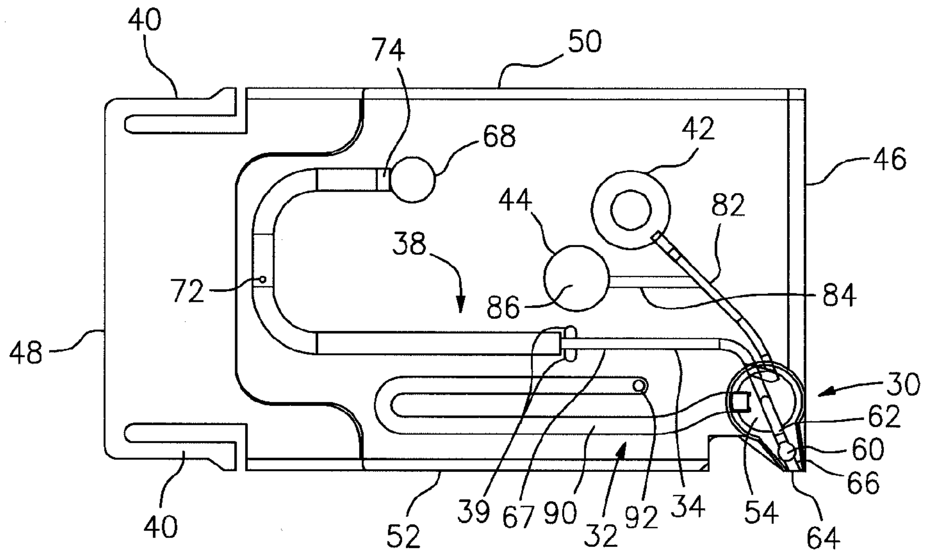
FIG. 7 is a planar view of a fluid module.

The external air port 44 is disposed within the fluid module 24 adjacent the air pressure source 42 (see FIG. 7). An airway 84 connects the external air port 44 to the airway 82 extending to the initial channel 34. The external air port 44 is configured to receive an air source associated with the analysis device 22 that selectively provides pressurized air, or draws a vacuum. A cap 86 (e.g., rupturable membrane) seals the external air port 44 to prevent the passage of gas or liquid there through prior to the external air source being connected to the external air port 44. In some embodiments, the cartridge 20 includes only an external air port 44 and does not include an air pressure source 42.

Figure 15:
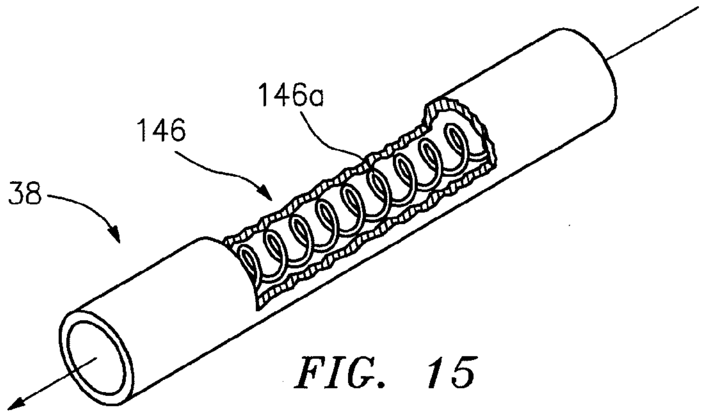
FIG. 15 is a diagrammatic perspective of a secondary channel showing a flow disrupter embodiment disposed within the channel.
Figure 16:
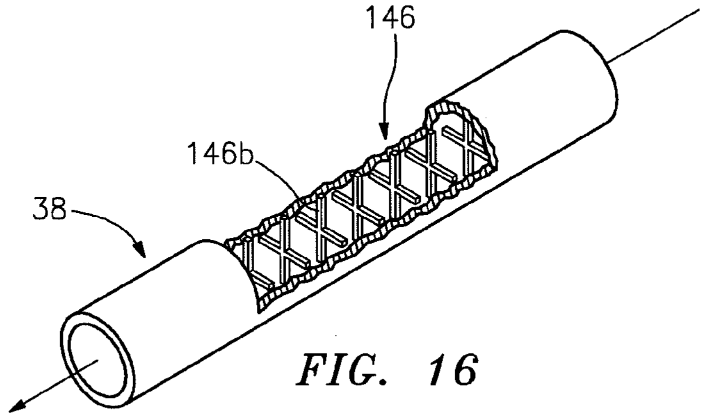
FIG. 16 is a diagrammatic perspective of a secondary channel showing a flow disrupter embodiment disposed within the channel.

In some embodiments, the cartridge 20 includes one or more sample flow disrupters configured in, or disposed within, one or both of the initial channel 34 and the secondary channel 38. In the embodiments shown in FIGS. 15-16, the disrupters are structures 146 disposed within the secondary channel 38 that are shaped to disrupt the flow of sample within the secondary channel 38. Under normal flow conditions, the disruption is sufficient to cause constituents within the sample to be distributed within the sample in a substantially uniform manner. An example of a disrupter structure 146 is a wire coil **146*a* having varying diameter coils (see FIG. 15). In another example, a disrupter structure 146 has a plurality of crossed structures 146*b* (e.g., "+") connected together (see FIG. 16). These are examples of flow disrupter structures 146** and the present invention is not limited to these examples.

Figure 17:
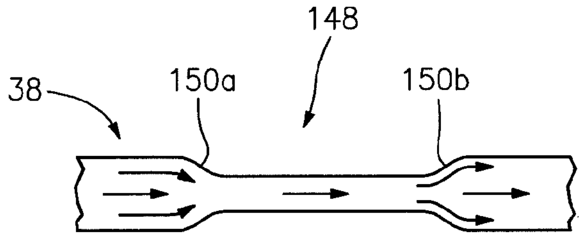
FIG. 17 is a diagrammatic perspective of a secondary channel showing a channel geometry variation embodiment.

In some embodiments (see FIGS. 17-18), one or both of the channels 34, 38 is configured to include a sample flow disrupter 146 in the form of a channel geometry variation that disrupts sample flowing within the secondary channel 38 under normal operating conditions (e.g., velocity, etc). The disruption is sufficient to cause constituents to be at least substantially uniformly distributed within the sample. For example, the secondary channel 38 embodiment shown in FIG. 17 has a portion 148 with a contracted cross-sectional area. Each end of the contracted portion 148 has a transition area **150*a*, 150*b* in which the cross-sectional area of the secondary channel 38 transitions from a first cross-sectional geometry to a second cross-sectional geometry. Fluid flowing within the secondary channel 38 encounters the first transition area 150*a* and accelerates as it enters the contracted portion 148, and subsequently decelerates as it exits the contracted portion through the second transition area 150*b*. The area rate of change within the transition areas 150*a*, 150*b* and the difference in cross-sectional area between the contracted portion 146 and the adjacent portions of the secondary channel 38 can be altered to create a desirable degree of non-laminar flow (e.g., turbulent) within the sample; e.g., the more abrupt the transition areas 150*a*, 150*b*** and the greater the difference in the cross-sectional areas, the greater the degree of turbulent flow. The degree to which the sample flow is turbulent (e.g., non-laminar) can be tailored to create the amount of mixing desired for a given sample analysis application.

Figure 18:
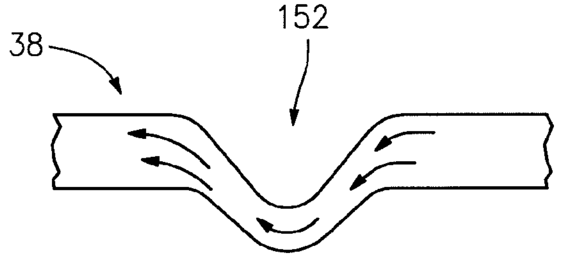
FIG. 18 is a diagrammatic perspective of a secondary channel showing a channel geometry variation embodiment.

FIG. 18 illustrates another example of channel geometry variation 152 that disrupts sample flowing within the secondary channel 38. In this example, the channel follows a curvilinear path (rather than a straight line path) that creates turbulent sample flow as the flow changes direction within the curvilinear path. The degree and rate at which the curvilinear path deviates from a straight line path will influence the degree to which the flow is turbulent; e.g., the more the path deviates, and/or the rate at which it deviates, the greater the degree of the turbulence within the sample flow.

Now referring back to FIGS. 7-10, the overflow passage 32 includes an inlet 88, a channel 90, and an air exhaust port 92. The inlet 88 provides fluid communication between the passage 32 and the bowl 54. As can be seen in FIGS. 9 and 10, the inlet 88 is positioned at a height within the bowl 54 such that a predetermined volume of fluid can collect within the bowl 54 and fill the initial channel 34 before the fluid can enter the inlet 88. The channel 90 has a cross-sectional geometry that allows the sample fluid to be drawn into and through the channel 90 (e.g., by capillary action). The channel 90 has a volume that is adequate to hold all excess sample fluid anticipated in most applications. The air exhaust port 92 is disposed proximate an end of the channel 90 opposite the inlet 88. The air exhaust port 92 allows air disposed within the channel 90 to escape as excess sample is drawn into the channel 90.

The overflow channel 90, initial channel 34, airways 82, 84, and the secondary channel 38 are disposed internally, and are therefore enclosed, within the fluid module 24. The present invention fluid module 24 is not limited to any particular configuration. For example, the fluid module 24 may be formed from two mating panels joined together. Any or all of the aforesaid channels 34, 90, 38, and airways 82, 84 can be formed in one panel, both panels, or collectively between the panels. The fluid module 24 shown in FIGS. 2-4 has an outer surface 94 (i.e., a "top" surface). In some embodiments, one or more sections of the top panel 94 (e.g., the section disposed above the initial channel 34 and the secondary channel 38) or the other panel are clear so the presence of sample within the aforesaid channels 34, 38 can be sensed for control purposes. In some embodiments, the entire top panel 94 is clear, and decals 96 are adhered to portions of the panel 94.

Now referring to FIGS. 13 and 14, at least one of the fluid module latches 40 has a configuration that engages a feature 98 extending out from the housing 28, as will be described below. In some embodiments, each latch 40 is configured as a cantilevered arm having a tab 100 disposed at one end.

Figure 4:
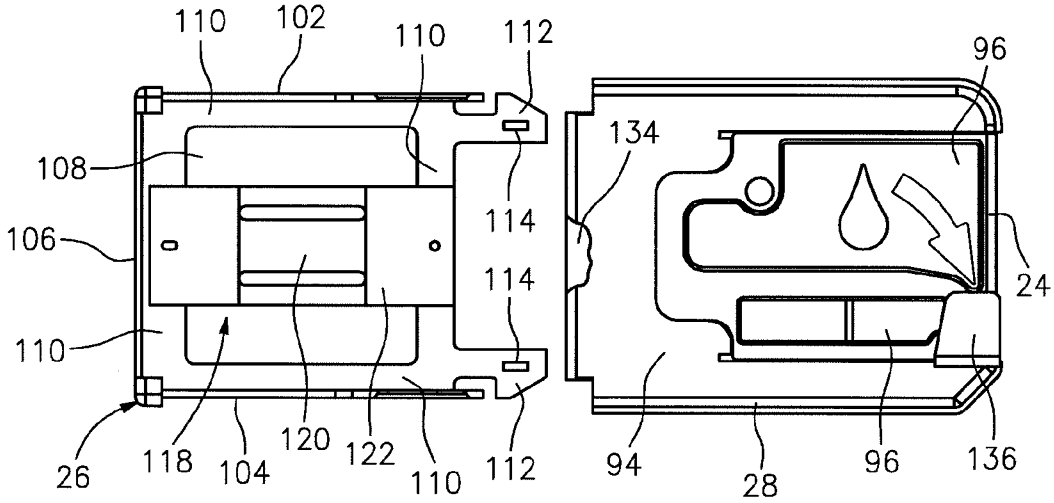
FIG. 4 is an exploded view of the cartridge embodiment, illustrating the imaging tray outside of the housing.

The Imaging Tray:

Now referring to FIG. 4, the imaging tray 26 includes a lengthwise extending first side rail 102, a lengthwise extending second side rail 104, and a widthwise extending end rail 106. The side rails 102, 104 are substantially parallel one another and are substantially perpendicular the end rail 106. The imaging tray 26 includes a chamber window 108 disposed in the region defined by the side rails 102, 104 and the end rail 106. A shelf 110 extends around the window 108, between the window 108 and the aforesaid rails 102, 104, 106.

Figure 20:
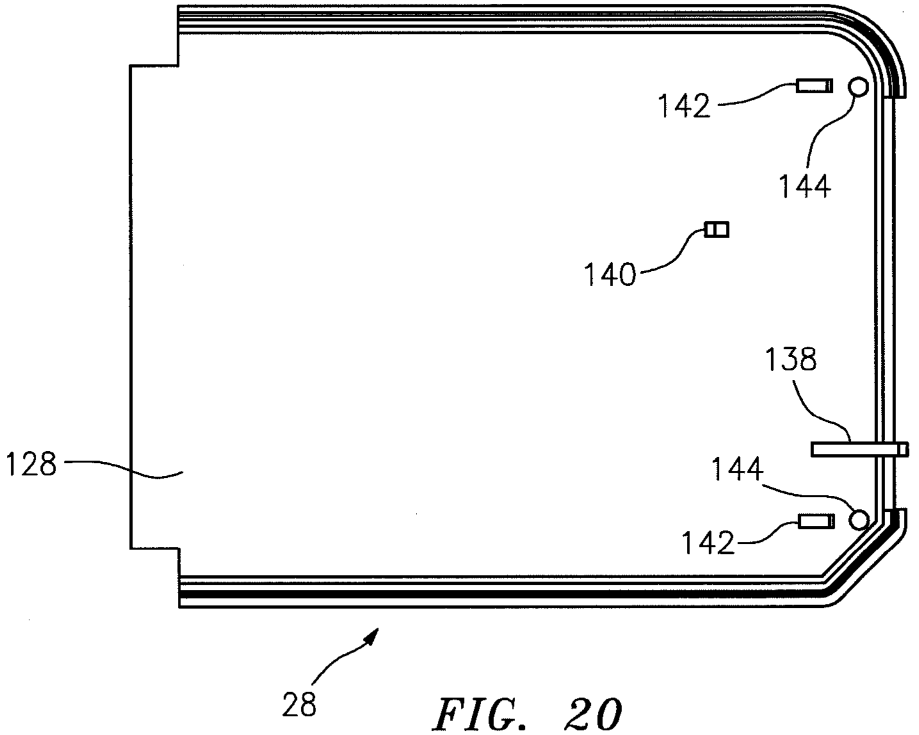
FIG. 20 is a planar view of a housing base.

The imaging tray 26 includes at least one latch member 112 that operates to selectively secure the imaging tray 26 within the housing 28. In the embodiment shown in FIG. 4, for example, a pair of latch members 112 cantilever outwardly from the shelf 110. Each latch member 112 includes an aperture 114 for receiving a tab 142 (see FIG. 20) attached to the interior of the housing 28. When the imaging tray 26 is received fully within the housing 28, the latch member apertures 114 align with and receive the tabs 142. As will be explained below, the housing 28 includes an access port 144 adjacent each tab. An actuator (e.g., incorporated within the analysis device 22) extending through each access port 144 can selectively disengage the latch member 112 from the tab 142 to permit movement of the imaging tray 26 relative to the housing 28.

A sample analysis chamber 118 is attached to the imaging tray 26, aligned with the chamber window 108. The chamber 118 includes a first panel 120 and a second panel 122, at least one of which is sufficiently transparent to permit a biologic fluid sample disposed between the panels 120, 122 to be imaged for analysis purposes. The first and second panels 120, 122 are typically substantially parallel one another, are substantially aligned with one another, and are separated from each other by a distance extending between the opposing surfaces of the two panels 120,122. The alignment between the panels 120, 122 defines an area wherein light can be transmitted perpendicular to one panel and it will pass through that panel, the sample, and the other panel as well, if the other panel is also transparent. The separation distance between the opposing panel surfaces (also referred to as the "height" of the chamber) is such that a biologic fluid sample disposed between the two surfaces will be in contact with both surfaces. One or both panels 120, 122 are attached (e.g., by welding, mechanical fastener, adhesive, etc.) to the shelf 110 disposed around the imaging tray window 108.

Figure 21A:
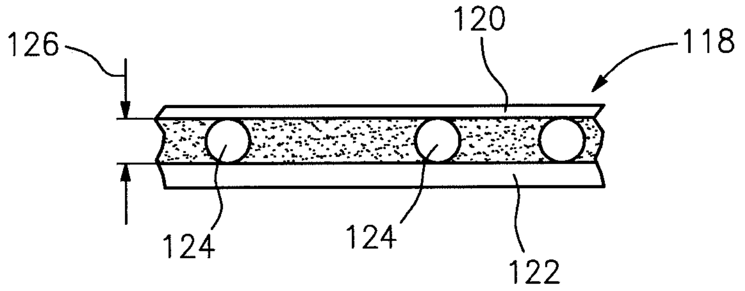
FIGS. 21A-21C are diagrammatic views of a sample chamber.
Figure 21B:
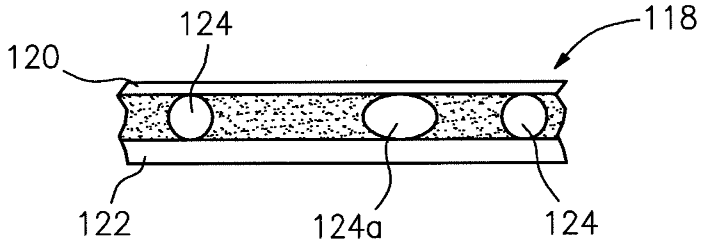
Figure 21C:
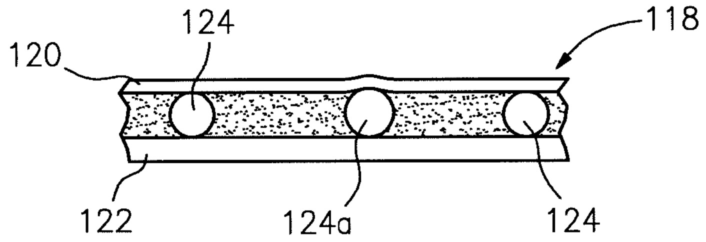

Now referring to FIGS. 21A-21C, an example of an acceptable chamber 118 is described in U.S. Patent Publication No. 2007/0243117, which is hereby incorporated by reference in its entirety. In this chamber embodiment, the first and second panels 120, 122 are separated by one another by at least three separators 124 (typically spherical beads). At least one of the panels 120, 122 or the separators 124 is sufficiently flexible to permit the chamber height 126 to approximate the mean height of the separators 124. The relative flexibility provides a chamber 118 having a substantially uniform height 126 despite minor tolerance variances in the separators 124. For example, in those embodiments where the separators 124 are relatively flexible (see FIG. 21B), the larger separators 124*a* compress to allow most separators 124 to contact the interior surfaces of the panels 120, 122, thereby making the chamber height 126 substantially equal to the mean separator diameter. In contrast, if the first panel 120 is formed from a material more flexible than the separators 124 and the second panel 122 (see FIG. 21C), the first panel 120 will overlay the separators and to the extent that a particular separator 124 is larger than the surrounding separators 124, the first panel 120 will flex around the larger separator 124 in a tent-like fashion. In this manner, although small local areas will deviate from the mean chamber height 126, the mean height of all the chamber sub-areas (including the tented areas) will be very close to that of the mean separator diameter. The capillary forces acting on the sample provide the force necessary to compress the separators 124, and/or flex the panel 120,122.

Examples of acceptable panel materials include transparent plastic film, such as acrylic, polystyrene, polyethylene terphthalate (PET), cyclic olefin copolymer (COC) or the like. One of the panels (e.g., the panel 122 oriented to be the bottom) may be formed from a strip of material with a thickness of approximately fifty microns (500, and the other panel (e.g., the panel 120 oriented to be the top panel) may be formed from the same material but having a thickness of approximately twenty-three microns (23*p*). Examples of acceptable separators 124 include polystyrene spherical beads that are commercially available, for example, from Thermo Scientific of Fremont, Calif., U.S.A., catalogue no. 4204A, in four micron (4 μm) diameter. The present cartridge is not limited to these examples of panels and/or separators.

The chamber 118 is typically sized to hold about 0.2 to 1.0 μl of sample, but the chamber 118 is not limited to any particular volume capacity, and the capacity can vary to suit the analysis application. The chamber 118 is operable to quiescently hold a liquid sample. The term "quiescent" is used to describe that the sample is deposited within the chamber 118 for analysis, and is not purposefully moved during the analysis. To the extent that motion is present within the blood sample, it will predominantly be due to Brownian motion of the blood sample's formed constituents, which motion is not disabling of the use of this invention. The present cartridge is not limited to this particular chamber 118 embodiment.

The Housing:

Now referring to FIGS. 3-6, 14, and 20, an embodiment of the housing 28 includes a base 128, a cover 130, an opening 132 for receiving the fluid module 24, a tray aperture 134, a bowl cap 136, a valve actuating feature 138, and an air source actuating feature 140. The base 128 and cover 130 attach to one another (e.g., by adhesive, mechanical fastener, etc.) and collectively form the housing 28, including an internal cavity disposed within the housing 28. Alternatively, the base 128 and cover 130 can be an integral structure. The opening 132 for receiving the fluid module 24 is disposed at least partially in the cover 130. The opening 132 is configured so that the top surface 94 of the fluid module 24 is substantially exposed when the fluid module 24 is received within the opening 132. Guide surfaces attached to (or formed in) one or both of the base 128 and the cover 130 guide linear movement of the fluid module 24 relative to the housing 28 and permit relative sliding translation. The guide surfaces include features 98 for engagement with the one or more fluid module latches 40. As will be explained below, the features 98 (see FIGS. 13-14) cooperate with latches 40 to limit lateral movement of the fluid module 24. The bowl cap 136 extends out from the cover 130 and overhangs a portion of the opening 132 (see FIGS. 2 and 6).

The valve actuating feature 138 extends out into the housing internal cavity at a position where the valve actuator 78 attached to the fluid module 24 will encounter the feature 138 as the fluid module 24 is slid into the housing 28. In a similar manner, the air source actuating feature 140 extends out into the internal cavity at a position where the pressure source actuator 80 attached to the fluid module 24 will encounter the feature 140 as the fluid module 24 is slid into the housing 28.

The imaging tray 26 is inserted into or out of the housing 28 through the tray aperture 134. Guide surfaces attached to (or formed in) one or both of the base 128 and the cover 130 guide linear movement of the imaging tray 26 relative to the housing 28 and permit relative sliding translation. The housing 28 includes one or more tabs 142, each aligned to engage an aperture 114 disposed within a latch member 112 of the imaging tray 26. The housing 28 further includes an access port 144 adjacent each tab 142. An actuator (incorporated into the analysis device 22) extending through each access port 144 can selectively disengage the latch member 112 from the tab 142 to permit movement of the imaging tray 26 relative to the housing 28.

The Analysis Device:

As stated above, the present biologic fluid sample cartridge 20 is adapted for use with an automated analysis device 22 having imaging hardware and a processor for controlling processing and analyzing images of the sample. Although the present cartridge 20 is not limited for use with any particular analytical device 22, an analysis device 22 similar to that described in U.S. Pat. No. 6,866,823 is an example of an acceptable device. To facilitate the description and understanding of the present cartridge 20, the general characteristics of an example of an acceptable analysis device 22 are described hereinafter.

The analysis device 22 includes an objective lens, a cartridge holding and manipulating device, a sample illuminator, an image dissector, and a programmable analyzer. One or both of the objective lens and cartridge holding device are movable toward and away from each other to change a relative focal position. The sample illuminator illuminates the sample using light along predetermined wavelengths. Light transmitted through the sample, or fluoresced from the sample, is captured using the image dissector, and a signal representative of the captured light is sent to the programmable analyzer, where it is processed into an image. The image is produced in a manner that permits the light transmittance (or fluorescence) intensity captured within the image to be determined on a per unit basis.

An example of an acceptable image dissector is a charge couple device (CCD) type image sensor that converts an image of the light passing through (or from) the sample into an electronic data format. Complementary metal oxide semiconductor ("CMOS") type image sensors are another example of an image sensor that can be used. The programmable analyzer includes a central processing unit (CPU) and is connected to the cartridge holding and manipulating device, sample illuminator and image dissector. The CPU is adapted (e.g., programmed) to receive the signals and selectively perforin the functions necessary to perform the present method.

Figure 5:
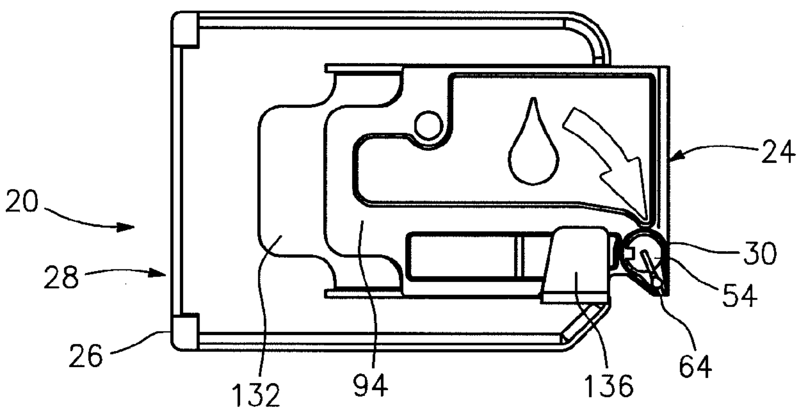
FIG. 5 shows the cartridge embodiment with the fluid module in an open position.
Figure 6:
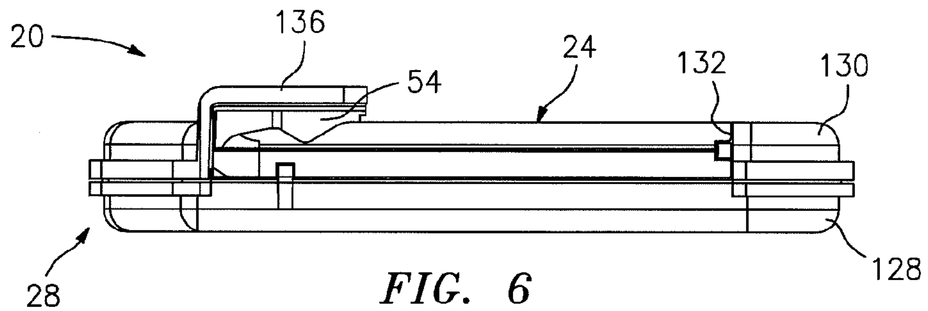
FIG. 6 is an end view of the cartridge embodiment.

Operation:

The present cartridge 20 is initially provided with the fluid module 24 set (or positionable) in an open position as is shown in FIGS. 5 and 13. In this position, the acquisition port 30 is exposed and positioned to receive a biologic fluid sample. The fluid module latches 40 engaged with the features 98 attached to the housing 28 maintain the fluid module 24 in the open position (e.g., see FIG. 13). When the fluid module 24 is disposed in the open position, the valve 36 is disposed in an open position wherein the fluid path between the sample intake 60 and the initial channel 34 is open.

A clinician or other end-user introduces a biological fluid sample (e.g., blood) into the inlet edge 64 or the bowl 54 from a source such as a syringe, a patient finger or heel stick, or from a sample drawn from an arterial or venous source. The sample is initially disposed in one or both of the channels 62, 66 and/or bowl 54, and is drawn into the sample intake 60 (e.g., by capillary action). In the event the amount of sample deposited into the bowl 54 is sufficient to engage the overflow passage inlet 88, capillary forces acting on the sample will draw the sample into the overflow channel 90. The sample will continue to be drawn into the shunt overflow passage 32 until the fluid level within the bowl 54 drops below the overflow passage inlet 88. Sample drawn into the overflow passage 32 will reside in the overflow channel 90 thereafter. The overflow exhaust port 92 allows air to escape as the sample is drawn into the channel 90.

Sample within the bowl 54 is drawn by gravity into the bowl-to-intake channel 62 disposed within the bowl base surface 58. Once the sample has entered the bowl-to-intake channel 62, and/or the inlet edge-to-intake channel 66, one or both of gravity and capillary forces will move the sample into the sample intake 60, and subsequently into the initial channel 34. Sample drawn into the initial channel 34 by capillary forces will continue traveling within the initial channel 34 until the front end of the sample "bolus" reaches the entrance to the secondary channel 38. In those embodiments where the initial channel 34 and/or a flag port 39 are visible to the end-user (including those assisted by a magnifier 41), the end-user will be able to readily determine that a sufficient volume of sample has been drawn into the cartridge 20. As indicated above, in certain embodiments of the present cartridge 20 one or more reagents 67 may be disposed around and within the initial channel 34 (e.g., heparin or EDTA in a whole blood analysis). In those embodiments, as the sample travels within the initial channel 34, the reagents 67 are admixed with the sample while it resides within the initial channel 34. The end-user subsequently slides the fluid module 24 into housing 28.

As the fluid module 24 is slid into the housing 28, a sequence of events occurs. First, the valve actuator 78 engages the valve actuating feature 138 as the fluid module 24 is slid inwardly. As a result, the valve 36 is actuated from the open position to the closed position, thereby preventing fluid flow between the sample intake 60 and initial channel 34. As the fluid module 24 is slid further into the housing 28, the pressure source actuator 80 engages the air source actuating feature 140 which causes the air pressure source 42 to increase the air pressure within the airway 82. The now higher air pressure acts against the fluid sample disposed within the initial channel 34, forcing at least a portion of the fluid sample (and reagent in some applications) into the secondary channel 38. The closed valve 36 prevents the sample from traveling back into the sample intake 60. As the fluid module 24 is slid completely into the housing 28, the tab 100 disposed at the end of each latch 40 engages the features 98 attached to the housing 28, thereby locking the fluid module 24 within the housing 28. In the locked, fully inserted position, the bowl cap 136 covers the sample intake 60. The fluid module 24 is thereafter in a tamper-proof state in which it can be stored until analysis is performed. The tamper-proof state facilitates handling and transportation of the sample cartridge 20. In those embodiments without an air pressure source 42, the sample may reside within the initial channel 34 during this state.

After the end-user inserts the cartridge 20 into the analysis device 22, the analysis device 22 locates and positions the cartridge 20. There is typically a period of time between sample collection and sample analysis. In the case of a whole blood sample, constituents within the blood sample (e.g., RBCs, WBCs, platelets, and plasma) can settle and become non-uniformly distributed. In such cases, there is considerable advantage in mixing the sample prior to analysis so that the constituents become substantially uniformly distributed within the sample. To accomplish that, the external air port 44 disposed in the fluid module 24 is operable to receive an external air source probe provided within the analysis device 22. The external air source provides a flow of air that increases the air pressure within the airways 82, 84 and initial channel 34, and consequently provides a motive force to act on the fluid sample. The external air source is also operable to draw a vacuum to decrease the air pressure within the airways 82, 84 and initial channel 34, and thereby provide a motive force to draw the sample in the opposite direction. The fluid sample can be mixed into a uniform distribution by cycling the sample back and forth within either or both of the initial channel 34 and the secondary channel 38. In those embodiments that include one or more disrupters 146 configured in, or disposed within, one or both of the initial channel 34 and the secondary channel 38. The flow disrupter facilitates the mixing of the constituents (and/or reagents) within the sample. Depending upon the application, adequate sample mixing may be accomplished by passing the sample once past the flow disrupter 146. In other applications, the sample may be cycled as described above.

In some embodiments, adequate sample mixing may be accomplished by oscillating the entire cartridge at a predetermined frequency for a period of time. The oscillation of the cartridge may be accomplished for example, by using the cartridge holding and manipulating device disposed within the analysis device 22, or an external transducer, etc.

After a sufficient amount of mixing, the external air source is operated to provide a positive pressure that pushes the fluid sample to a position aligned with the metering port 72 and beyond, toward the distal end of the secondary channel 38. The gas permeable and liquid impermeable membrane 74 disposed adjacent the exhaust port 68 allows the air within the chamber 38 to escape, but prevents the fluid sample from escaping. As the fluid sample travels within the secondary channel 38 and encounters the sample metering port 72, capillary forces draw a predetermined volume of fluid sample into the sample metering port 72. The pressure forces acting on the sample (e.g., pressurized air within the channel that forces the sample to the distal end of the channel) cause the sample disposed within the metering port 72 to be expelled from the metering port 72.

When both the imaging tray 26 and the fluid module 24 are in a closed position relative to the housing 28 (e.g., see FIG. 2), the sample metering port 72 is aligned with a portion of the bottom panel 122 of the analysis chamber 118, adjacent an edge of the top panel 120 of the chamber 118. The sample is expelled from the metering port 72 and deposited on the top surface of the chamber bottom panel 122. As the sample is deposited, the sample contacts the edge of the chamber 118 and is subsequently drawn into the chamber 118 by capillary action. The capillary forces spread an acceptable amount of sample within the chamber 118 for analysis purposes.

The imaging tray latch member 112 is subsequently engaged by an actuator incorporated into the analysis device 22 to “unlock” the imaging tray 26, and the imaging tray 26 is pulled out of the housing 28 to expose the now sample-loaded analysis chamber 118 for imaging. Once the image analysis is completed, the imaging tray 26 is returned into the cartridge housing 28 where it is once again locked into place. The cartridge 20 can thereafter be removed by an operator from the analysis device 22. In the closed position (see e.g., FIG. 2), the cartridge 20 contains the sample in a manner that prevents leakage under intended circumstances and is safe for the end-user to handle.

In an alternative embodiment, the imaging tray can be “locked” and “unlocked” using a different mechanism. In this embodiment, the latch member(s) 112 also cantilevers outwardly from the shelf 110 and includes the aperture 114 for receiving the tab 142 (or other mechanical catch) attached to the interior of the housing 28. In this embodiment, the latch member further includes a magnetically attractable element. A magnetic source (e.g., a magnet) is provided within the analysis device 22. To disengage the latch member 112, the magnetic source is operated to attract the element attached to the latch 112. The attraction between the magnetic source and the element causes the cantilevered latch to deflect out of engagement with the tab 142, thereby permitting movement of the imaging tray 26 relative to the housing 28.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention. As an example of such a modification, the present cartridge 20 is described as having an external air port 44 disposed within the fluid module 24 for receiving an external air source. In alternative embodiments, a source of air pressure could be included with the fluid module 24; e.g., a gas bladder disposed within the fluid module 24 that can produce positive and negative air pressures when exposed to a thermal source. As another example of a modification, the present invention cartridge is described above as having a particular embodiment of an analysis chamber 118. Although the described cartridge embodiment is a particularly useful one, other chamber configurations may be used alternatively. As a still further example of a modification, the present cartridge is described above as having particular latch mechanisms 40, 112. The invention is not limited to these particular latch embodiments.

What is claimed is:

1. A biological fluid sample analysis cartridge, comprising:

a fluid module having a sample acquisition port, an initial channel, and a second channel, and which initial channel is sized to draw fluid sample by capillary force, and which initial channel is in fluid communication with the acquisition port and is fixedly positioned relative to the acquisition port such that at least a portion of a fluid sample disposed within the acquisition port will draw into the initial channel; and an analysis chamber attached to an imaging tray, which imaging tray is slidably received within the cartridge and selectively positionable relative to the cartridge in a first position and in a second position, and in the second position the analysis chamber is positioned to receive fluid from the secondary channel; and wherein the secondary channel is fluidically disposed between the initial channel and the analysis chamber such that fluid sample exiting the initial channel must pass through the secondary channel before entering the analysis chamber; and wherein an intersection between the initial channel and the secondary channel prevents capillary forces from drawing sample out of the initial channel and into the secondary channel.

2. The cartridge of claim 1, wherein at least a portion of one or both of the initial channel and the secondary channel is visible from the top surface.

3. The cartridge of claim 1, wherein the acquisition port includes a bowl, and the housing includes a bowl cap that is sized to cover the bowl.

4. The cartridge of claim 1, further comprising an external air port in fluid communication with the initial channel, which external air port is configured to engage an air source operable to produce air at a pressure greater than and/or less than ambient air pressure.

5. The cartridge of claim 1, further comprising one or more flow disrupters disposed within one or both of the initial channel and the secondary channel.

6. The cartridge of claim 1, further comprising a channel geometry variation in one or both of the initial and secondary channels, which variation is operable to create turbulent sample fluid flow within at least one of the initial channel or the secondary channel.

7. The cartridge of claim 1, wherein the initial channel has a volume, and the cartridge further comprises an overflow passage, which overflow passage is disposed to receive fluid sample when a volume of fluid sample introduced into the acquisition port exceeds the volume of the initial channel.

8. The cartridge of claim 7, wherein the overflow passage is sized to draw fluid sample into the overflow passage by capillary force.

9. The cartridge of claim 1, further comprising one or more flag ports in fluid communication with the initial channel, which flag ports are configured to receive fluid sample and visually indicate the presence of the fluid sample.

10. The cartridge of claim 1, further comprising at least one magnifier section, which magnifier section includes a lens that magnifies a view of the initial channel or a view of a flag port.

11. The cartridge of claim 1, wherein in the first position the analysis chamber is visible for analysis and in the second position the analysis chamber is not visible for analysis.

12. The cartridge of claim 11, wherein the imaging tray is selectively lockable in the second position, in which position it is disposed within the cartridge.

13. The cartridge of claim 1, wherein the analysis chamber includes a first panel and a second panel, at least one of which panels is sufficiently transparent to permit fluid sample disposed between the panels to be imaged for analysis purposes.

* * * * *